United States Patent [19]

Rosenberger

[11] 4,055,539

[45] Oct. 25, 1977

[54] ALKYLIDENE-BISPHENOLS CONTAINING SULPHUR, AND THEIR USE AS STABILIZERS

[75] Inventor: Siegfried Rosenberger, Riehen, Switzerland

[73] Assignee: Ciba-Geigy Corporation, Ardsley, N.Y.

[21] Appl. No.: 690,470

[22] Filed: May 27, 1976

Related U.S. Application Data

[63] Continuation-in-part of Ser. No. 610,498, Sept. 4, 1975, abandoned.

[30] Foreign Application Priority Data

Sept. 16, 1974 Switzerland ............... 12573/74

[51] Int. Cl.$^2$ .................. C08K 5/05; C08K 5/13; C07C 149/36
[52] U.S. Cl. .................. 260/45.95 C; 260/810; 260/609 F

[58] Field of Search .................. 260/609 F, 45.95 B, 260/810

[56] References Cited

U.S. PATENT DOCUMENTS

| 2,398,253 | 4/1946 | Rogers et al. | 260/609 F |
| 2,937,208 | 5/1960 | Retter et al. | 260/609 F |
| 3,060,121 | 10/1962 | Orloff et al. | 260/609 F |
| 3,506,716 | 4/1970 | Peterli et al. | 260/609 F |
| 3,644,649 | 2/1972 | Fuchsman | 260/609 F |

FOREIGN PATENT DOCUMENTS

| 1,116,127 | 2/1967 | United Kingdom | 260/609 F |

*Primary Examiner*—Delbert R. Phillips
*Attorney, Agent, or Firm*—Nestor W. Shust

[57] ABSTRACT 1,1-Bis-(3-alkyl-2-hydroxyphenyl)-3-alkylthio-butanes to -pentadecanes in which the alkyl, which is in the 3-position, is not branched at the α-carbon atom, are good stabilizers for elastomers.

9 Claims, No Drawings

ALKYLIDENE-BISPHENOLS CONTAINING SULPHUR, AND THEIR USE AS STABILIZERS

This application is a continuation-in-part application of our parent application Ser. No. 610,498, filed Sept. 4, 1975. now abandoned.

1,1′-Bis-(2-hydroxy-3,5-dialkylphenyl)-methylenes which contain a tertiary alkyl group in the 3-position and which are used as antioxidants for rubber, are known from U.S. Pat. No. 2,796,444. British patent specification No. 1,116,127 describes, as stabilisers for polyolefines, 1,1-bis-(3,5-dialkyl-2-hydroxyphenyl)-3-thioalkyl-propanes in which the alkyl group, which is in the 3-position, is branched at the α-carbon atom.

The present invention relates to compounds of the general formula I

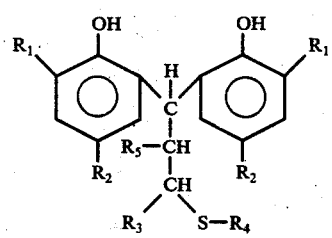

(I)

wherein $R_1$ denotes an alkyl group which has 1 to 18 carbon atoms and which is not branched in the α-position, $R_2$ denotes a linear or branched alkyl group having 1 to 8 carbon atoms, or a hydrogen atom, $R_3$ denotes an alkyl group having 1 to 6 carbon atoms and $R_5$ denotes a hydrogen atom or an alkyl group having 1 to 6 carbon atoms, and $R_4$ denotes a linear or branched alkyl group having 1 to 20 carbon atoms wherein the carbon chain can be interrupted by sulphur atoms.

In the formula I, $R_1$ is preferably an alkyl group which has 1 to 8, particularly 1 to 4 carbon atoms, and which is not branched at the α-carbon atom, and $R_2$ is preferably an alkyl group having 1 to 4 carbon atoms.

The alkyl radical $R_4$, which is interrupted by sulphur, is preferably composed in such a way that at least 2 carbon atoms are linked between 2 sulphur atoms. $R_4$ is particularly preferentially an alkyl radical, particularly an alkyl radical having 4 to 16 carbon atoms.

$R_3$ is preferably alkyl having 1 to 4 carbon atoms. Preferably, $R_3$ and $R_5$ are, independently of one another, each a methyl group or $R_5$ also a hydrogen atom, in particular $R_3$ is a methyl group and $R_5$ is a hydrogen atom.

Particularly valuable compounds of the formula I are those in which $R_1$ denotes the methyl or ethyl group and $R_2$ preferably denotes an alkyl radical having 1 to 4 carbon atoms, particularly also the methyl or ethyl group.

In formula I $R_1$ and $R_2$ particularly preferentially represent the methyl group and $R_4$ preferably represents an alkyl radical having 4 to 16 carbon atoms.

The compounds of the formula I are new and are obtained by process which are in themselves known, by reacting, in the presence of an acid catalyst, a phenol of the formula II (II)

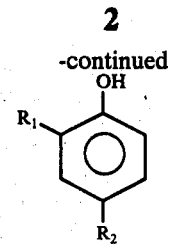

wherein $R_1$ and $R_2$ have the same meaning as in formula I, with a thioaldehyde of the formula III

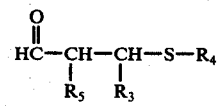

(III)

wherein $R_3$ and $R_4$ and $R_5$ have the same meaning as in formula I. Known processes are, for example, described in British patent specification No. 1,116,127. In general, about 2 mols of phenol are used here to about 1 mol of thioaldehyde.

Examples of catalysts which can be used are: hydrogen chloride, sulphuric acid, zinc chloride or trifluoroacetic acid. The reaction can be carried out with or without a solvent.

Examples of suitable solvents are: aliphatic and aromatic hydrocarbons, halogenated aliphatic and aromatic hydrocarbons, alcohols or ethers.

It is preferable to employ as the catalyst a liquid Lewis acid etherate-adduct which acts at the same time as the reaction medium. Particularly good yields are achieved here if at least 3 mols of the liquid catalyst are used per mol of reaction product.

The following should be mentioned as Lewis acids which are suitable for the formation of ether-adducts: aluminium trihalides and boron trihalides, for example aluminium trifluoride, trichloride and tribromide and boron trifluoride and trichloride.

Preferred catalysts are adducts formed from boron trifluoride and ethers, particularly diethyl ether.

The aldehydes of the formula III are obtained by carrying out an addition reaction, in the presence of a base such as triethylamine, between mercaptans $R_4SH$, the radical $R_4$ having the same meaning as in formula I, and corresponding unsaturated aldehydes.

Examples of compounds of the formula I are: 1,1-bis-(3,5-dimethyl-2-hydroxyphenyl)-3-(n-dodecylthio)-n-butane, 1,1-bis-(3,5-dimethyl-2-hydroxyphenyl)-3-(n-octylthio)-n-butane, 1,1-bis-(3-ethyl-5-methyl-2-hydroxyphenyl)-3-(n-octadecylthio)-n-butane, 1,1-bis-(3-methyl-5-n-butyl-2-hydroxyphenyl)-3-(n-octylthio)-n-butane, 1,1-bis-(3-methyl-5-tert.-butyl-2-hydroxyphenyl)-3-(n-octylthio)-n-butane, 1,1-bis-(3-n-octyl-5-isopropyl-2-hydroxyphenyl)-3-n-hexadecylthio)-n-butane, 1,1-bis-(3-octadecyl-5-methyl-2-hydroxyphenyl)-3-(ethylthio)-n-butane, 1,1-bis-[3-methyl-5-(2-ethylhexyl)-2-hydroxyphenyl]-3-(n-eicosylthio)-n-butane, 1,1-bis-(3-butyl-5-n-octyl-2-hydroxyphenyl)-3-(n-heptadecylthio)-n-butane, 1,1-bis-(3-methyl-5-ethyl-2-hydroxyphenyl)-2-n-hexyl-3-(n-tridecylthio)-n-butane, and 1,1-bis-(3,5-dimethyl-2-hydroxyphenyl)-3-(n-hexylthio)-n-nonane.

The compounds of the formula I are used as stabilisers for elastomers, such as, for example, natural rubber, polybutadiene, ethylene-propylene copolymers, propylene-butene-1 copolymers, propylene-isobutylene copolymers, styrene-butadiene copolymers, and terpolymers of ethylene and propylene with a diene, such as, for example, hexadiene, dicyclopentadiene or ethylidenenorbornene; and styrene polymers which have been modified by rubber phases so as to be impact-resistant, such as acrylonitrile/butadiene/styrene, acrylonitrile/styrene, or acrylic ester copolymers.

In this field the compounds of the formula I, according to the invention, have, surprisingly, a better action than compounds which are structurally closely related, which are described in British patent specification No. 1,116,127.

The compounds of the formula I are incorporated in the substrates in a concentration of 0.005 to 5% by weight, relative to the material to be stabilised.

Preferably, 0.01 to 1.0, particularly preferably 0.02 to 0.5, % by weight of the compounds, relative to the material to be stabilised, are incorporated into the latter. The incorporation can be carried out, for example, by mixing in at least one of the compounds of the formula I and optionally further additives by the methods customary in the art, before or during shaping, or by applying the compounds, dissolved or dispersed, to the polymer, where appropriate with subsequent evaporation of the solvent. The compounds of the formula I can also be added before or during the polymerisation.

The following may be mentioned as examples of further additives with which the stabilisers can be conjointly employed:

1. Antioxidants 1.1. Simple 2,6-dialkylphenols, such as, for example, 2,6-ditert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2. Derivatives of alkylated hydroquinones, such as, for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxyanisole, tris-(3,5-di-tert.-butyl-4-hydroxyphenyl) phosphite, 3,5-di-tert.-butyl-4-hydroxyphenyl stearate and bis-(3,5-di-tert.-butyl-4-hydroxyphenyl) adipate.

1.3. Hydroxylated thiodiphenyl ethers, such as, for example, 2,2'-thio-bis-(6-tert.-butyl-4-methylphenol), 2,2'-thio-bis-(4-octylphenol), 4,4-thio-bis-(6-tert.-butyl-3-methylphenol), 4,4'-thio-bis-(3,6-di-sec.-amylphenol), 4,4'-thio-bis-(bis-(2,6-dimethyl-4-hydroxyphenol)-disulphide.

1.4. Alkylidene-bisphenols, such as, for example, 2,2'-methylene-bis-(6-tert.butyl-4-methylphenol), 2,2'-methylene-bis-(6-tert.butyl-4-ethylphenol), 4,4'-methylene-bis-(6-tert. butyl-2-methylphenol), 4,4'-methylene-bis-(2,6-di-tert. butyl-phenol), 2,6-di-(3-tert. butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl) butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert.butyl-4-hydroxy-2-methylphenyl)-4-n-dodecylmercaptobutane, 1,1,5,5-tetra-(5-tert.butyl-4-hydroxy-2'-methylphenyl)-pentane and ethylene-glycol-bis-[3,3-bis-(3'-tert.butyl-4-hydroxyphenyl)-butyrate].

1.5. O-, N- and S-benzyl compounds, such as, for example, 3,5,3',5'-tetra-tert.butyl-4,4'-dihydroxydibenzyl ether, 4-hydroxy-3,5-dimethylbenzyl-mercaptoacetic acid octadecyl ester, tris-(3,5-di-tert.butyl-4-hydroxybenzyl)-amine and bis-(4-tert.butyl-3-hydroxy-2,6-dimethylbenzyl) dithioterephthalate.

1.6. Hydroxybenzylated malonic esters, such as, for example, 2,2-bis-(3,5-di-tert.butyl-2-hydroxybenzyl)-malonic acid dioctadecyl ester, 2-(3-tert.butyl-4-hydroxy-5-methylbenzyl)-malonic acid dioctadecyl ester, 2,2-bis-(3,5-di-tert.butyl-4-hydroxybenzyl)-malonic acid di-dodecylmercapto-ethyl ester and 2,2-bis-(3,5-di-tert.butyl-4-hydroxybenzyl)-malonic acid di-[4-(1,1,3,3-tetramethylbutyl)-phenyl]-ester.

1.7. Hydroxybenyl-aromatic compounds, such as, for example, 1,3,5-tri-(3,5-di-tert.butyl-4-hydroxybenzyl)-2,4,6-trimethylbenzene, 1,4-di-(3,5-di-tert.butyl-4-hydroxybenzyl-2,3,5,6-tetramethylbenzene and 2,4,6-tri-(3,5-di-tert.butyl-4-hydroxybenzyl)-phenol.

1.8. s-Triazine compounds, such as, for example, 2,4-bis-octylmercapto-6-(3,5-di-tert.butyl-4-hydroxyanilino)-s-triazine, 2-octylmercapto-4,6-bis-(3,5-di-tert.butyl-4-hydroxy-anilino)-s-triazine, 2-octylmercapto-4,6-bis-(3,5-di-tert.butyl-4-hydroxy-phenoxy)-s-triazine, 2,4,6-tris-(3,5-di-tert.butyl-4-hydroxy-phenoxy)-s-triazine, 2,4,6-tris-(3,5-di-tert.butyl-4-hydroxyphenylethyl)-s-triazine and 1,3,5-tris-(3,5-di-tert.-butyl-4-hydroxybenzyl) isocyanurate.

1.9 Amides of β-(3,5-di-tert.butyl-4-hydroxyphenyl)-propionic acid, such as, for example, 1,3,5-tris-(3,5-di-tert.butyl-4-hydroxyphenyl-propionyl)-hexahydro-s-triazine and N,N'-di-(3,5-di-tert.butyl-4-hydroxyphenyl-propionyl)-hexamethylenediamine.

1.10 Esters of β-(3,5-di-tert.butyl-4-hydroxyphenyl)-propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2,]octane.

1.11. Esters of β-(5-tert.butyl-4-hydroxy-3methylphenyl)-propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo [2,2,2,]octane.

1.12. Esters of 3,5-di-tert.butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2,2,2,]octane.

1.13. Benzylphosphonates, such as, for example, 3,5-di-tert. butyl-4-hydroxybenzyl-phosphonic acid dimethyl ester, 3,5-di-tert.butyl-4-hydroxybenzyl-phosphonic acid diethyl ester, 3,5-di-tert.butyl-4-hydroxybenzyl-phosphonic acid dioctadecyl ester and 5-tert.butyl-4-hydroxy-3-methylbenzyl-phosphonic acid dioctadecyl ester.

1.14. Aminoaryl derivatives, such as, for example, phenyl-1-naphthylamine, phenyl-2-naphthylamine, N,N'-diphenyl-p-phenyl-enediamine, N,N'-di-2-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydroquino-line, monooctyliminodibenzyl and dioctyliminodibenzyl and polymerised 2,2,4-trimethyl-1,2-dihydroquinoline. Octylated diphenylamine, nonylated diphenylamine, N-phenyl-N'-cyclohexyl-p-phenylenediamine, N-phenyl-N'-isopropyl-p-phenylenediamine, N,N'-di-sec.octyl-p-phenylenediamine, N-phenyl-N'-sec.octyl-p-phenylenediamine, N,N'-di-(1,4-dimethylpentyl)-p-phenylene-diamine, N,N'-dimethyl-N,N'-di-(sec.octyl)-p-phenylenediamine, 2,6-dimethyl-4-methoxyaniline, 4-ethoxy-N-sec.-butylaniline, the condensation product of diphenylamine and acetone, and phenothiazine.

2. UV absorbers and light stabilisers 2.1. 2-(2-Hydroxyphenyl)-benztriazoles, such as, for example, the 5'-methyl-, 3',5'-di-tert.butyl-, 5'-tert.butyl-, 5'-(1,1, 3,3-tetramethylbutyl)-, 5-chloro-3',5'-di-tert.butyl-, 5-chloro-3'-tert.butyl-5'-methyl-, 3'-sec.butyl-5'-tert.butyl-, 3'-α-methylbenzyl-5'-methyl-, 3'-α-methylbenzyl-5'-methyl- 5-chloro-,4'-hydroxy-, 4'-methoxy-, 4'-octoxy-, 3',5'-di-tert.amyl-, 3'-methyl-5'-carbomethoxyethyl- or 5chloro-3',5'-di-tert.-amyl-derivative.

2.2. 2.4-Bis-(2'-hydroxyphenyl)-6-alkyl-s-triazines, such as, for example, the 6-ethyl-, 6-heptadecyl- or 6-undecyl-derivative.

2.3. 2-Hydroxy-benzophenones, such as, for example, the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivative.

2.4. 1,3-Bis-(2'-hydroxy-benzoyl)-benzenes, such as, for example, 1,3-bis-(2'-hydroxy-4'-hexyloxy-benzoyl)-benzene, 1,3-bis-(2'-hydroxy-4'-octyloxy-benzoyl)-benzene and 1,3-bis-(2'-hydroxy-4'-dodecyloxy-benzoyl)-benzene.

2.5. Esters of optionally substituted benzoic acids, such as, for example, phenyl salicylate, octylphenyl salicylate, dibenzoyresorcinol, bis-(4-tert.-butylbenzoyl)-resorcinol, benzoyl-resorcinol and 3,5-di-tert.-butyl-4-hydroxybenzoic acid 2,4-di-tert.butyl-phenyl ester, octadecyl ester of 2-methyl-4,6-di-tert.butyl-phenyl ester.

2.6. Acrylates, such as, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester and N-(β-carbomethoxy-vinyl)-2-methyl-indoline.

2.7. Nickel compounds, such as, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel complexes of bis-[2-hydroxy-4-(1,1,3,3-tetramethylbutyl)-phenyl]-sulphone, such as the 2:1 complex, optionally with additional ligands such as 2-ethyl-caproic acid, nickel dibutyldithiocarbamate, nickel salts of 4-hydroxy-3,5-di-tert.butylbenzyl-phosphonic acid monoalkyl esters, such as of the methyl, ethyl or butyl ester, nickel complexes of ketoximes such as of 2-hydroxy-4-methyl-phenyl-undecylketonoxime, nickel 3,5-di-tert.-butyl-4-hydroxy-benzoate and nickel isopropylxanthate.

2.8. Sterically hindered amines, such as, for example, 4-benzoyloxy-2,2,6,6-tetramethylpiperidine, 4-stearoyloxy-2,2,6,6-tetramethylpiperidine, bis-(2,2,6,6-tetramethylpiperidyl) sebacate, and 3-n-octyl-7,7,9,9-tetramethyl-1,3,8-triaza-spiro[4,5]decane-2,4-dione.

2.9. Oxalic acid diamides, such as, for example, 4,4'-di-octyloxy-oxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis-(3-dimethylaminopropyl)-oxalamide, 2-ethoxy-5-tert.butyl-2'-ethyl-oxanilide and its mixture with 2-ethoxy-2'-ethyl-5,4'-di-tert.butyl-oxanilide and mixtures of ortho- and para-methoxy as well as of o-and p-ethoxy-disubstituted oxanilides.

3. Metal deactivators, such as, for example, oxanilide, isophthalic acid dihydrazide, sebacic acid bis-phenylhydrazide, bis-benzylidene-oxalic acid dihydrazide, N,N'-diacetyl-adipic acid dihydrazide, N,N'-bis-salicyloyl-oxalic acid dihydrazide, N,N'-bis-salicyloyl-hydrazine, N,N'-bis-(3,5-di-tert.butyl-4-hydroxyphenyl-propionyl)-hydrazine, N-salicylal-N'-salicylidenehydrazine and 3-salicyloylamino-1,2,4-triazole.

4. Phosphites, such as, for example, triphenyl phosphite, diphenylalkyl phosphites, phenyldialkyl phosphites, tri-(nonyl-phenyl) phosphite, trilauryl phosphite, trioctadecyl phosphite, 3,9-di-isodecyloxy-2,4,8,10-tetroxa-3,9-diphospha-spiro [5,5]-undecane and tri-(4-hydroxy-3,5-di-tert.butylphenyl) phosphite.

5. Compounds which destroy peroxides, such as, for example, esters of β-thiodipropionic acid, for example the lauryl, stearyl, myristyl or tridecyl esters, mercapto-benzimidazole and the zinc salt of 2-mercapto-benzimidazole.

6. Nucleating agents, such as, for example, 4-tert.butyl-benzoic acid, adipic acid and diphenylacetic acid.

7. Other additives, such as, for example, plasticisers, lubricants, emulsifiers, fillers, carbon black, asbestos, kaolin, talc, glass fibres, pigments, optical brighteners, flameproofing agents and antistatic agents.

The preparation and use of the compounds which can be used in accordance with the invention are described in greater detail in the examples which follow. In these, parts denote parts by weight and percentages denote percentages by weight.

A. Preparation of the compounds

Examples 1–4

1,1-Bis-(3,5-dimethyl-2-hydroxyphenyl)-3-(n-dodecylthio)-n-butane 27.2 g of 3-(n-dodecylthio)-butanal-1 are added, over the course of 10 hours at 0°–5° C, to 24.4 g of 2,4-dimethylphenol and 46.9 g of boron trifluoride ethyl-etherate and the reaction mixture is stirred for a further 24 hours at room temperature. A white paste of crystals is formed, which is treated with 70 ml of methanol while stirring and cooling. The suspension is warmed to 50° C for half an hour and cooled once more and the crystals are filtered off.

The product is purified by washing successively with methanol, water and again methanol and is dried at 40° C.

This gives 1,1-bis-(3,5-dimethyl-2-hydroxyphenyl)-3-(n-dodecylthio)-n-butane (stabiliser No. 1) in the form of white crystals of melting point 106°–108° C.

The corresponding thia-alkylidene-bisphenols are obtained if the 3-(n-dodecylthio)-butanal-1 in the previous example is replaced by one of the thia-aldehydes in Table 1 which follows.

Table 1

| Example | Stabiliser No. | Thia-aldehyde | Thio-alkylidene-bisphenol | Melting point |
|---------|----------------|---------------|---------------------------|---------------|
| 2 | 2 | $\text{HC}(=O)-\text{CH}_2\text{CH}(\text{CH}_3)-\text{S}-n\text{-C}_4\text{H}_9$ | 1,1-Bis-(3,5-dimethyl-2-hydroxyphenyl)-3-(n-butylthio)-n-butane | 103° C |
| 3 | 3 | $\text{HC}(=O)-\text{CH}_2\text{CH}(\text{CH}_3)-\text{S}-n\text{-C}_8\text{H}_{17}$ | 1,1-Bis-(3,5-dimethyl-2-hydroxyphenyl)-3-(n-octylthio)-n-butane | 116° C |
| 4 | 4 | $\text{HCCH}_2(=O)-\text{CH}(\text{CH}_2\text{CH}_2\text{CH}_3)-\text{S}-n\text{-C}_{12}\text{H}_{25}$ | 1,1-Bis-(3,5-dimethyl-2-hydroxyphenyl)-3-(n-dodecylthio)-n-hexane | Approx. 50° C (purified by column chromatography) |

When isolating the compounds of Examples 2 – 5 above, consideration must be given under certain circumstances to the fact that the tendency of the substances to crystallise varies greatly. If appropriate, ice water must be added to the reaction mixture and the organic phase must be washed until it is neutral and must be dried, after which it can be converted into the crystalline products either by evaporation and treatment with methanol or by purification by column chromatography.

EXAMPLE 5

1,1-Bis(3-methyl-5-tert.-butyl-2-hydroxyphenyl)-3-(n-octylthio)-n-butane

If, in Example 1, the 2,4-dimethylphenol is replaced by 2-methyl-4-tert.-butylphenol, an identical procedure gives 1,1-bis-(3-methyl-5-tert.butyl-2-hydroxyphenyl)-3-n-octyl-thio)-n-butane (stabiliser No. 5) in the form of a viscous oil, which is freed from by-products by column chromatography.

The elementary analysis agrees with the formula indicated.

EXAMPLE 6

1,1-Bis-(3-ethyl-5-tert.-butyl-2-hydroxyphenyl)-3-(n-dodecylthio)-n-butane

If, in Example 1, the 2,4-dimethylphenol is replaced by 2-ethyl-4-tert.-butylphenol, an identical procedure gives 1,1-bis-(3-ethyl-5-tert.-butyl-2-hydroxyphenyl)-3-(n-dodecylthio)-n-butane (stabiliser No. 6) in the form of a viscous oil, which is freed from by-products by column chromatography.

B. Technological Examples

Examples 7–11

Stabilisation of Polybutadiene Rubber 100 parts of polybutadiene ("Solprene 250" of Messrs. Phillips), which is pre-stabilised with 0.36% of 2,6-ditert.-butyl-p-cresol, are kneaded for 30 minutes in a Brabender plastograph at 150° C and 60 revolutions/minute with an additional 0.1 part of each of the stabilisers shown in Table 2. The resistance to kneading is continuously registered in the form of the torque during this time. A maximum occurs in the torque owing to crosslinking which sets in initially, and subsequent degradation. The effectiveness of the stabilisers is expressed by a reduction in the torque maximum.

The gel content which can be determined after the Brabender treatment is considered a further criterion of the protective action of the stabilisers incorporated. For this purpose, 1 g of the sample is dissolved overnight at room temperature in 100 ml of toluene. These solutions are filtered through glass wool, the gel particles which are retained are rinsed with a little toluene and the filtered solutions are evaporated to dryness and are dried to a constant weight. The gel content of a sample is obtained from the following calculation:

Gel content in % = $(E - A/E) \times 100$
$E$ = total weight of the sample tested
$A$ = weight of the dissolved fraction.

In Examples 9–11 known stabilisers have been used for comparison.

Table 2

| Example | Stabilizer | Torque maximum in gramme × meter | Gel content (%) |
|---------|------------|----------------------------------|-----------------|
| 7 | Without stabilizer | 3,625 | 44 |
| 8 | 1 | 1,980 | 0 |
| 9 | 2,6-Di-tert.-butyl-4-methyl-1-hydroxyphenol | 3,350 | 35 |
| 10 | 2,2'-Methylene-bis-(6-tert.-butyl-4-methyl phenol) | 3,550 | 33 |
| 11 | 1,1-Bis-(2-methyl-5-tert.-butyl-4-hydroxyphenyl)-3-(n-octadecylthio)-n-butane | 3,250 | 35 |

EXAMPLES 12–14

Stabilisation of Polybutadiene Rubber 100 parts of polybutadiene ("Solprene 250" of Messrs. Phillips), which is pre-stabilised with 0.36% of 2,6-ditert.-butyl-p-cresol, are homogenised in a Brabender plastograph for 10 minutes at 150° C and 60 revolutions/minute with an additional 0.1 part of one of the stabilisers shown in Table 3. The mixtures stabilised in this way are pressed into test pieces 10 mm thick for 5 minutes in a press at 120° C. The test piece of non-stabilised rubber which serves for comparison is prepared in the same manner.

The Mooney value which is determined after storage in the atmosphere at elevated temperatures, is considered a criterion of the protective action of the stabiliser incorporated. For this purpose, the test samples are kept at 150° C on aluminium supports in a circulating air oven and their Mooney value is determined after 20 hours. (DIN 53523,ASTM D 927-57 T). The Mooney value is understood as the torque which has to be applied to turn a cylindrical disc (rotor) at a speed of revolution of 2 revolutions/minute in a chamber filled with the sample. The value is read off at a temperature of 100° C after the rotor has been running for a period of 4 minutes. Higher Mooney values denote cross-linking of the plastic and hence damage caused by the aging in the oven.

Table 3

| Stabiliser No. | Mooney value | Torque |
|---|---|---|
| None | 128 | 1.08 kp × m |
| 1 | 48 | 0.40 kp × m |
| 3 | 48 | 0.40 kp × m |

EXAMPLES

Stabilisation of Polybutadiene Rubber 0.1 percent by weight of the stabilisers as listed in Table 4 were incorporated in a rolling-mill at 40°–50° C in polybutadiene (Solprene 250 and for another sample Cariflex 1202 of Shell). The mixtures are pressed then into test pieces of 10 mm thickness in a press for 20 minutes at 80° C.

The time in hours of increasing of the Moony-Viscosity to more then 10 points is taken as the criterion of the protective action. The higher time is the better is the effectiveness. For this purpose the test samples are aged at 150° C on aluminium supports in a circulating air oven. From time to time there are measured 25 gramm samples of the stock according to the procedure as described in Examples 13–15.

The gel content is determined as described in Examples 8 to 12.

The test data is given in Table 4.

All residues in Table 4 are referred to the following general formula.

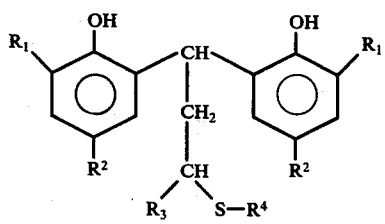

From this results it can be seen that the compounds according to the invention in which the hydroxyl group is connected in the o-position, the $R_1$-group is linear alkyl and $R_3$ is alkyl of 1 to 6 carbons are surprisingly for superiour in their effectiveness as compared to closest prior art compounds (e.g. U.S. Pat. No. 3,506,716).

From examples 16, 18, 20, 22 and 24 it can be seen that the length of the residue $R_4$ do not greatly influence the effectiveness. A comparison of examples 11 and 24 demonstrate therefore with respect to the gel content that the o-hydroxy-compounds are more effective than the p-hydroxy compounds.

A comparison of examples 16 and 17, 18 and 19, 20 and 21 demonstrate that the effectiveness is much more higher when the $R_3$-group denotes an alkyl residue, and a comparison of examples 20, 24 and 25 demonstrate the great superiority when $R_1$ denote a linear alkyl group.

The greater effectiveness of the stabilisers according to the invention is surprising which results from the inventive combination of the new features, especially the non-obvious selection of the o-hydroxy-compounds with linear alkyl groups in the $R_1$-position together with the replacement of a hydrogen atom in the $R_4$-position by an alkyl group.

What we claim is:

1. A compound of the general formula I

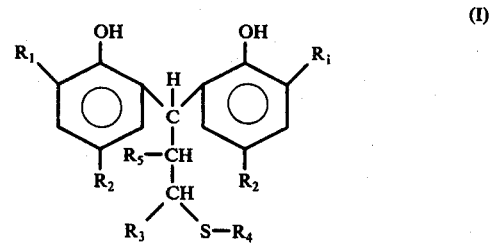

wherein $R_1$ is an alkyl group which has 1 to 18 carbon atoms and which is not branched in the α-position, $R_2$ denotes a linear or branched alkyl group having 1 to 8 carbon atoms, or a hydrogen atom, $R_3$ denotes an alkyl group having 1 to 6 carbon atoms and $R_5$ denotes a hydrogen atom or an alkyl group having 1 to 6 carbon atoms, and $R_4$ denotes a linear or branched alkyl group having 1 to 20 carbon atoms wherein the carbon chain can be interrupted by sulphur atoms.

2. A compound according to claim 1, characterised in that $R_4$ is an alkyl radical having 4 to 16 carbon atoms.

3. A compound according to claims 1, characterised in that $R_1$ is a methyl or ethyl group.

Table 4

| Example | Stabiliser No. | $R_1$ | $R_2$ | $R_3$ | $R_4$ | Gel content in % Cariflex 2002 | Gel content in % Solprene 250 | Oven going at 150° C time of increasing of Mooney Viscosity to about 10 minutes (Solprene 250) |
|---|---|---|---|---|---|---|---|---|
| 15 | none | — | — | — | — | 50 | 51 | 3 |
| 16 | 2 | $CH_3$ | $CH_3$ | $CH_3$ | $n$-$C_4H_9$ | — | 0 | 19 |
| 17 | Comparison | $CH_3$ | $CH_3$ | H | $n$-$C_4H_9$ | — | 37 | 8 |
| 18 | 3 | $CH_3$ | $CH_3$ | $CH_3$ | $n$-$C_8H_{17}$ | — | 0 | 18–24 |
| 19 | Comparison | $CH_3$ | $CH_3$ | H | $n$-$C_8H_{17}$ | — | 48 | 7 |
| 20 | 1 | $CH_3$ | $CH_3$ | $CH_3$ | $n$-$C_{12}H_{25}$ | 0 | 0 | 18–24 |
| 21 | Comparison | $CH_3$ | $CH_3$ | H | $n$-$C_{12}H_{25}$ | — | >50 | 6 |
| 22 | 4 | $CH_3$ | $CH_3$ | n-propyl | $n$-$C_{12}H_{25}$ | — | 0 | 20 |
| 23 | Comparison | $CH_3$ | H | $CH_3$ | $n$-$C_{12}H_{25}$ | 33 | 40 | 8 |
| 24 | 5 | $CH_3$ | tert.-butyl | $CH_3$ | $n$-$C_8H_{17}$ | 0 | 0–8 | 15 |
| 25 | Comparison | tert.-butyl | tert.-butyl | $CH_3$ | $n$-$C_{12}H_{25}$ | 9 | 12 | 6–8 |

4. A compound according to claims 1, characterised in that $R_3$ denotes alkyl of 1 to 4 carbon atoms and $R_5$ denotes a hydrogen atom or a methyl group.

5. A compound according to claims 1, characterised in that $R_1$ and $R_2$ represent the methyl group.

6. A compound according to claim 1 of the formula I, which is 1,1-bis-(3,5-dimethyl-2-hydroxyphenyl)-3-(n-dodecylthio)-n-butane.

7. A stabilised mixture according to claim 1 consisting of a) an elastomer and b) 0.005 to 5% by weight of at least one of the compounds of the formula I, relative to the elastomer.

8. A Mixture according to claim 7, characterised in that it contains 1,1-bis-(3,5-dimethyl-2-hydroxyphenyl)-3-(n-dodecylthio)-n-butane as the compound of the formula I.

9. A mixture according to claim 7, wherein the elastomer is natural rubber or polybutadiene.

* * * * *